Figure 1:
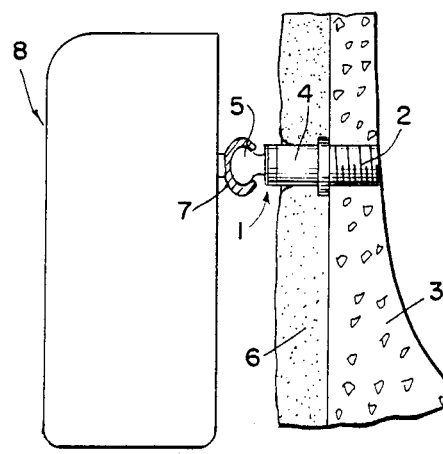

United States Patent [19]

Hakansson

[11] Patent Number: 4,498,461
[45] Date of Patent: Feb. 12, 1985

[54] COUPLING TO A BONE-ANCHORED HEARING AID

[76] Inventor: Bo Hakansson, Sanatoriegatan 27, Göteborg, Sweden, 416 53

[21] Appl. No.: 522,161
[22] PCT Filed: Dec. 1, 1982
[86] PCT No.: PCT/SE82/00411
    § 371 Date: Jul. 26, 1983
    § 102(e) Date: Jul. 26, 1983
[87] PCT Pub. No.: WO83/02047
    PCT Pub. Date: Jun. 9, 1983

[30] Foreign Application Priority Data
Dec. 1, 1981 [SE] Sweden .................. 8107161

[51] Int. Cl.³ .................. H04R 25/00; A61F 1/24
[52] U.S. Cl. .................. 128/1 R; 179/107 BC; 181/126
[58] Field of Search .................. 128/1 R; 179/107 BC; 181/126

[56] References Cited
U.S. PATENT DOCUMENTS

| | | | |
|---|---|---|---|
| 3,594,514 | 7/1971 | Wingrove | 128/1 R X |
| 3,751,605 | 8/1973 | Michelson | 128/1 R X |
| 4,052,754 | 10/1977 | Homsy | 128/1 R X |
| 4,071,110 | 1/1978 | Payne | 179/107 BC X |
| 4,352,960 | 10/1982 | Dorner et al. | 179/107 BC |

Primary Examiner—Edward M. Coven
Attorney, Agent, or Firm—Holman & Stern

[57] ABSTRACT

The present invention refers to a coupling intended for mechanical transmission of sound information from a vibration generating apparatus as a transmitter to the skull of a person with damaged hearing, including a first coupling part, for example directly anchored to the skull, and a second coupling part attachable to it and mounted on the sender, whereby at least one vibration-transmitting surface is formed between the coupling parts.

3 Claims, 15 Drawing Figures

FIG. 6a
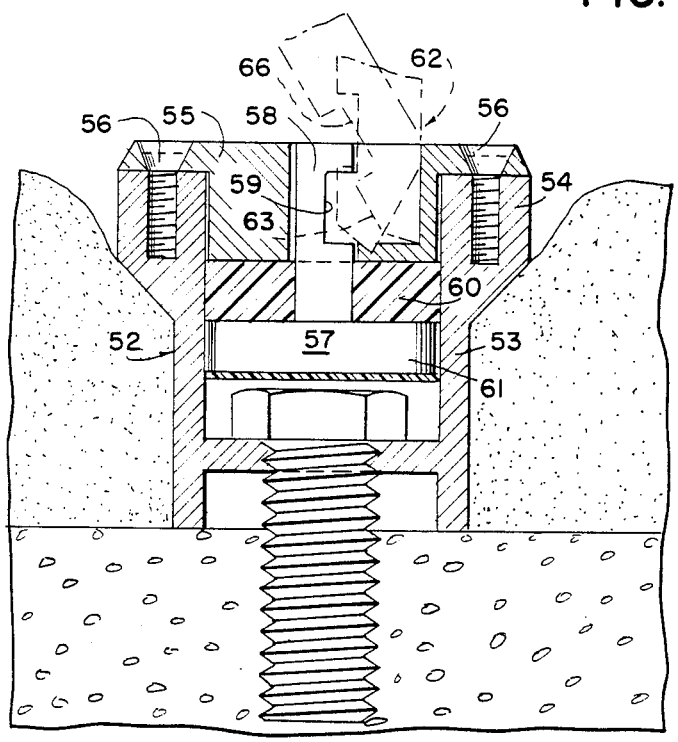
FIG. 6c
FIG. 6b
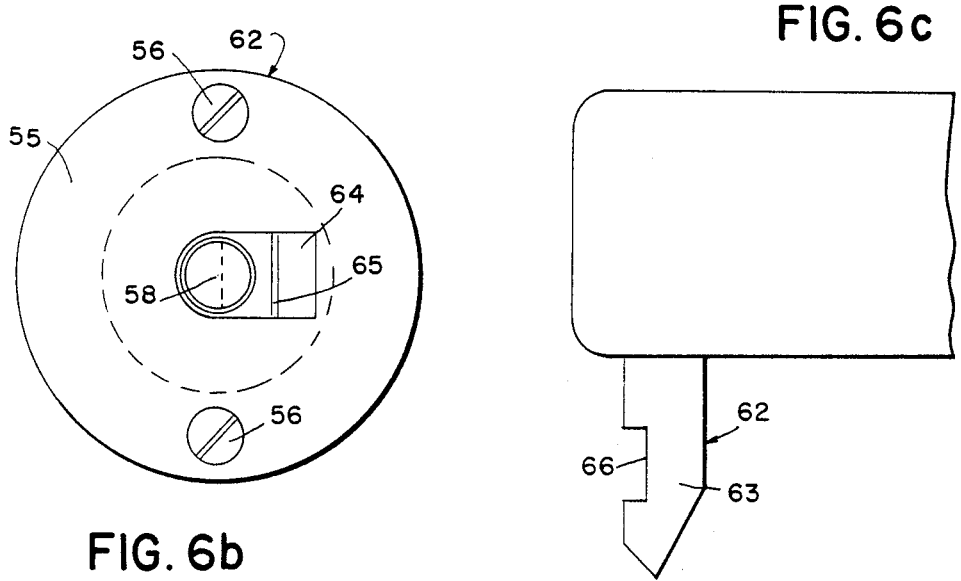

COUPLING TO A BONE-ANCHORED HEARING AID

CROSS REFERENCE TO RELATED APPLICATION(S)

The United States application stems from PCT International application No. PCT/SE82/00411 filed Dec. 1, 1982.

The present invention refers to a coupling intended for mechanical transmission of sound information from a vibration generating apparatus as a transmitter to the skull of a person with damaged hearing, including a first coupling part, for example directly anchored to the skull, and a second coupling part attachable to it and mounted on the sender, whereby at least one vibration transmitting surface is formed between the coupling parts.

BACKGROUND OF THE INVENTION AND TECHNOLOGICAL STATUS

Perhaps the most common hearing damage today takes the form of defects in the inner ear which usually are corrected with different types of hearing aids attached to the external ear canal. Certain patients who need hearing aids cannot use conventional hearing aids which transmit air-borne sound through that canal but instead must use a bone-conduction hearing apparatus. The reasons can be several. For example the hearing canal, can be defective, perhaps already from birth, so that the air-borne sound is not passed while the organs of the inner ear are intact. Experience has shown that the inner ear is very sensitive to sound in the form of vibrations which are transmitted through the skull. A transmitter which generates sound vibrations is then attached to the side of the head, for example using a steel spring over the head, in the region of the ear and transmits sound via the head skin and bone to the inner ear. The pressure with which the transmitter is applied against the head in order to obtain as good mechanical contact as possible is uncomfortable for the patient. In addition the skin and tissue cause damping of the vibrations especially in the high frequencies. During recent years through improved medical techniques one can permanently implant a metallic skin penetration which is anchored in the skull for transmission of sound by vibrations. Because no damping skin is present between the sender and the skull a considerably better sound transmission is obtained while simultaneously the electrical current used by the sender can be reduced. In addition esthetic improvements have been obtained because the steel spring over the head is not needed.

A known coupling is available on the market today and is shown in FIG. 1. It includes ball-shaped and cup-shaped coupling parts of which one, for example the ball-shaped part, is attached to the skull behind the ear of the patient. The coupling part penetrates the skin and sticks out 4–6 mm outside the skin. To that coupling part the sender with its cup-shaped coupling part is attached with a "snap lock."

This known coupling has a number of drawbacks. For example the ball-shaped coupling part sticking out of the head causes several inconveniences. In addition to purely esthetic drawbacks clothing can easily catch on the ball. In spite of the fact that the part of the coupling in contact with tissue (skull bone, skin) is made of titanium, which has shown very good characteristics concerning ingrowth with the bone, the skull bone can be damaged by strong mechanical loading such as blows and the like. The problem is accentuated by the fact that the coupling comprises a not inconsiderable lever by virtue of its large physical height. This is also a problem during sleep when the coupling can be in the way or catch on the bedclothes.

Other problems, such as that the coupling unscrews itself and falls out, have appeared during practical use. For example experience has shown that the mechanical contact between the coupling parts is weakened in time which results in reduced sound quality in the transmission. This is because distortion results at certain frequencies and sound strengths and the coupling parts are not able to maintain the mechanical contact. Further drawbacks are that the coupling is not provided with a "neutral position" which means that the transmitter, which is often asymmetrically formed, can slip around the contact ball and lie against the skin which can cause interference and discomfort for the patient.

THE PURPOSE OF THE INVENTION AND ITS PRIMARY CHARACTERISTICS

The purpose of the present invention is to eliminate the aforementioned drawbacks and to achieve a coupling which is esthetically attractive, easy to use, inexpensive to manufacture and easy to apply and repair. This is achieved thereby that the vibration transmitting surface or surfaces of the first coupling part is/are arranged inside the outer surface of the first coupling part.

SHORT DESCRIPTION OF THE FIGURES

The invention will be described in the following in an embodiment with reference to the attached figures.

Figure 2A:
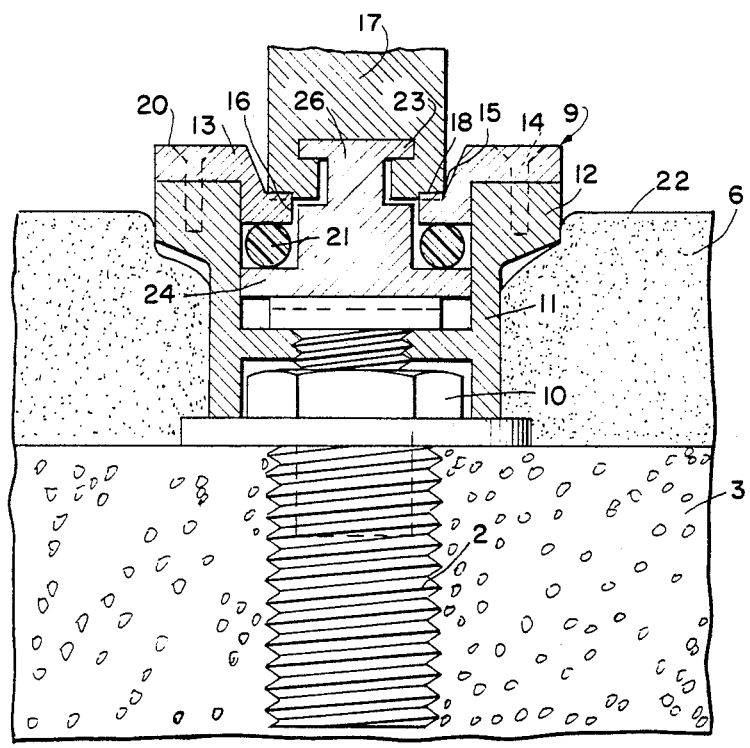
Figure 2B:
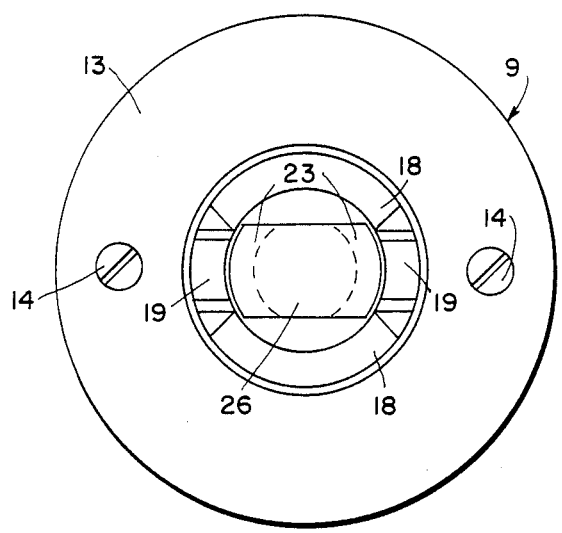
Figure 3A:
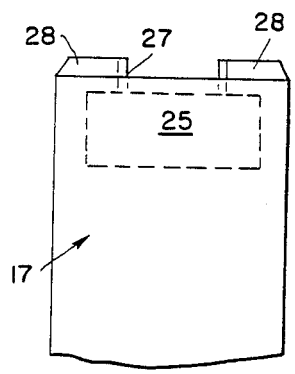
Figure 4A:
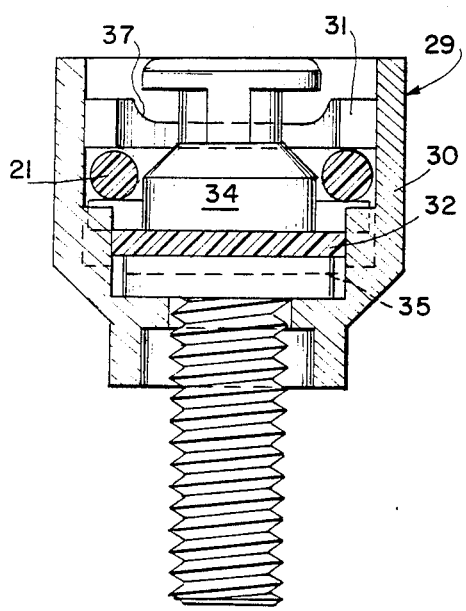
Figure 3B:
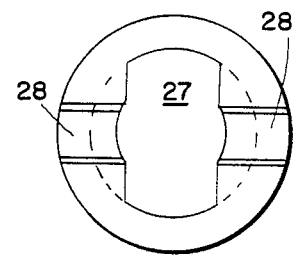
Figure 4B:
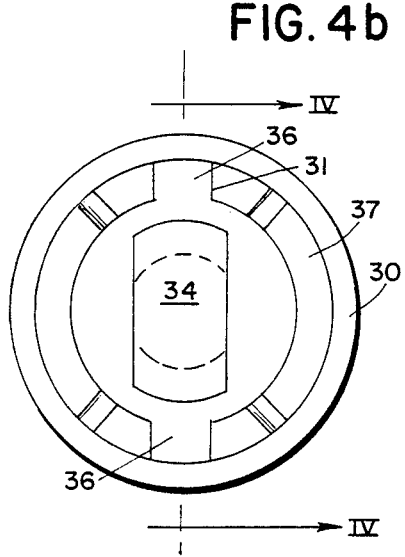
Figures 5A, 5B:
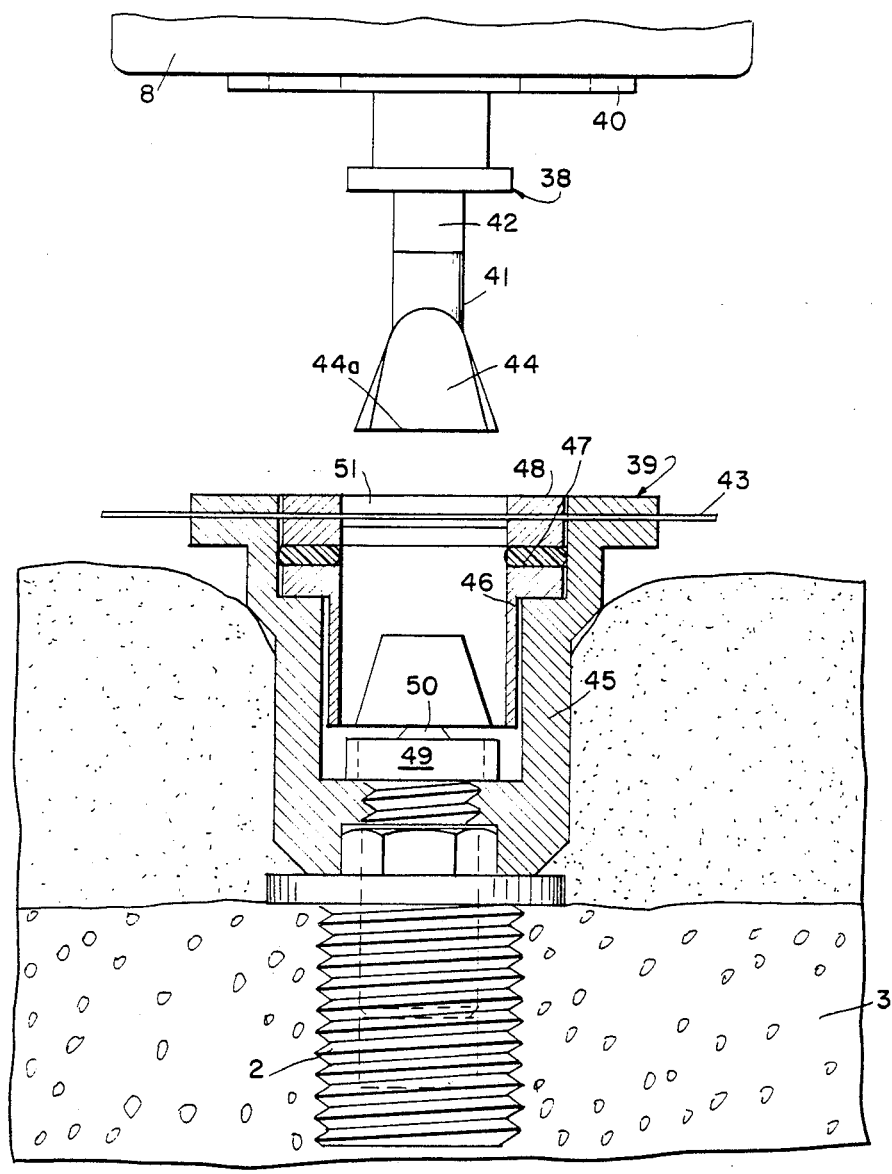
Figure 7A:
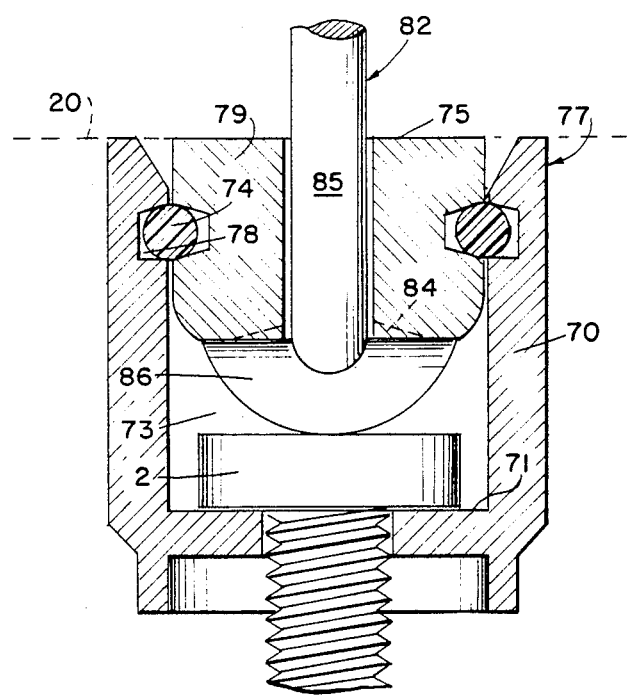
Figure 7B:
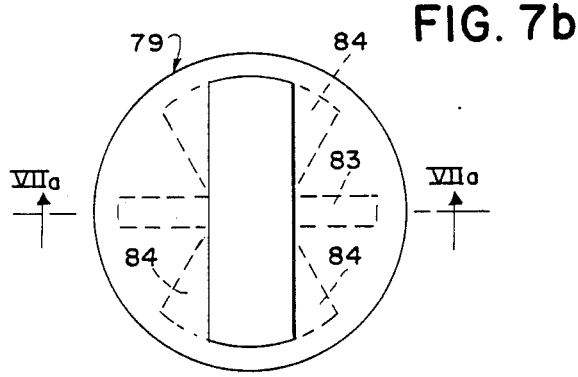
Figure 7C:
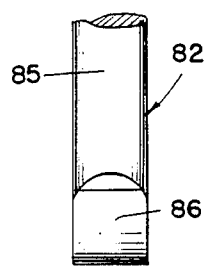

FIG. 1 shows a view, partly in cross section, of a known coupling,

FIG. 2a shows a cross section through the first coupling part of a coupling according to the invention, FIG. 2b shows the first coupling part according to FIG. 2a from above, FIG. 3a shows a second coupling part which fits the first coupling part shown in FIGS. 2a and 2b, FIG. 3b shows the second coupling part, according to FIG. 3a, from above, FIG. 4a shows a cross section through an alternative first coupling part, intended to be connected to the second coupling part shown in FIG. 3a,b, FIG. 4b shows the first coupling part according to FIG. 4a, from above, FIG. 5a shows a cross-section through a further embodiment of a coupling according to the invention, and more exactly its first coupling part, FIG. 5b shows a second coupling part which fits the first coupling part shown in FIG. 5a, FIG. 6a shows a further embodiment of a first coupling part, FIG. 6b shows the first coupling part according to FIG. 6a, from above, FIG. 6c shows a second coupling part which fits the first coupling part according to FIGS. 6a and 6b, FIG. 7a shows a cross-section of a coupling with parts which can easily be separated, FIG. 7b shows an insert spacer, placed in a coupling according to 7a, from above, FIG. 7c shows a coupling part, which fits the coupling shown in 7a, from the side.

DESCRIPTION OF EXAMPLE REALIZATIONS

In FIG. 1 is thus shown a known coupling 1 in an application. A bone screw 2 of titanium is threaded and healed into the skull 3 of a patient. In the bone screw 2, which has an internally threaded hole in its center, a spacer 4 is screwed tight and on its outer end is mounted a ball-shaped coupling part 5. Also the spacer 4 is made of titanium and extends from the bone screw 2 out through the skin 6. On the ball-shaped coupling part 5 a transmitter 8 is mounted via a cup-shaped coupling part 7, which transducer contains for example a microphone, amplifier, vibrator and battery. The thus constructed coupling 1 has a number of drawbacks which were discussed above.

In FIG. 2a is shown a coupling according to the invention and mainly the part that is to be mounted tightly in the skull of the patient. This part, which in the embodiment shown here consists of a first coupling part 9, is screwed tightly by a mounting screw 10 in a bone screw 2 of titanium in the same way as the known coupling. The bone screw is in turn surgically inserted into the skull bone of the patient, for example behind one ear. The first coupling part 9 contains mainly a cylindrical frame 11, equipped with a flange 12 at its upper end in which a front plate 13 is mounted tightly via for example two screws 14. The plate 13 can of course be mounted by other means such as glueing, riveting or the like. In the plate 13 is mounted a downward narrowing cup-formed part 15, in the center of which a rectangular volume 16 is made, and in which cup-shaped part 15 a second coupling part 17 can be inserted. Around the volume 16 in the cup-formed part's 15 bottom a circular path 18 is formed in which two grooves 19 are arranged opposite one another in which corresponding raised parts on the second coupling part 17 glide down on locking the coupling. The coupling parts are thus arranged to be locked to each other through rotation of either of the coupling parts, for example through a quarter turn, in relation to the other coupling part.

In the cylindrical frame 11 an active element 21 which is movable in the axial direction, under the front line, that is in an imaginary line at the same height as the plate 13 or the coupling part's outer surface 20, and a fastening element 26, made for example of tough plastic, are arranged. By active element 21 is meant here an arrangement which applies a mostly constant force which presses the coupling's 1 first and second coupling parts 9, 17 against one another in their coupled position. This force is strong enough that no distortion can occur between the coupling parts 9, 17. Because the active element 21, and for example also the vibration transmitting surface, that is the surface or the surfaces which are formed between the coupling parts 9, 17 and whose purpose is to transmit sound in the form of vibrations, is arranged at the level of or under the front line, the coupling's total physical height can be kept relatively low, and the coupling need not stick out unnecessarily outside the skin 6 but instead the front line of the coupling will be mostly at the level of the skin's 6 outer surface 22.

The fastening element 26 is stretched, with its upper part containing a gripping piece, through the volume 16 formed in the plate's 13 middle. The upper surface of the fastening element's gripping piece 23 is thus placed at the level of the coupling's outer surface 20. The gripping piece 26 which is mainly rotationally symmetrical, is equipped with a flange 24 at the bottom which forms a stop for the active element, an O-ring 21 of a flexible material, for example silicon rubber.

The upper stop or limit for this O-ring is formed by the plate's 13 under surface.

In FIG. 2b the first coupling part 9 is shown from above so that the grooves 19 in the plate 13 are clearly visible. The fastening element's 26 upper part, which contains a gripping piece 23, is flattened on two sides partly to allow insertion in the second coupling part's 17 gripping volume or chamber 25 and partly to keep the fastening element 26 from rotating inside the coupling which would cause the fastening piece's 16 and the plate's 13 positions relative to one another to change with the result that the coupling would be useless.

In FIG. 3a is shown transducer the second coupling part 17 which is mounted on the transducer. It is mainly rod-shaped and contains an internal cylindrical hole 25. A mainly rectangular shaped opneing 27 allows insertion of the fastener's 26 gripping pieces 23. On each long side of the opening are raised parts 28 arranged radially which glide with their outer surfaces along a path 18 and down in the grooves 19 at rotating and locking the coupling. Thus an advantageous self-cleaning of the vibration transmitting surface in the coupling is obtained so that mechanical contact can always be maintained.

FIG. 3b shows the outer end of the second coupling part 17 in such a way that the opening 27 and the raised parts 28 are clearly visible.

FIG. 4a shows an alternative first coupling part 29 in which the plate's 13 function is exchanged for a cylindrical internally arranged stop 31 inside the frame 30. Neither is the frame 30 equipped with a flange 12 above as no plate 13 with fastening screws 14 is used. Through this arrangement the outer diameter of the coupling can be reduced further. A packing 32 of for example silicon rubber is placed between the fastening element 34 and the bone screw 35 and is arranged to damp uncomfortable snapping sounds which can be produced when the parts are coupled together and to allow for mounting the O-ring and locking it.

FIG. 4b shows the alternative first coupling part 29 from above so that the fastening element 34, the grooves 36, the glide path 37 and the upper part of the frame 30 are visible.

In FIGS. 5a and 5b are shown an additional embodiment of the coupling according to the invention including a second coupling part 38 and a first coupling part 39. The second coupling part 38 consists of a plate 40 to which a transmitter 8 can be attached, an axle 41 equipped with a square part 42 arranged for coordination with a spring loaded pin 43 placed in the first coupling part 39 and a flattened contact part 44. The first coupling part 39 consists of an outer frame 45 in which a locking cylinder 46 made of a tough plastic, a flexible packing 47, of for example silicon rubber, and an outer plate 48 and two spring loaded pins 43 through it and at a distance from each other. At the bottom the first coupling part 39 is further equipped with a screw 49, to the upper part of which a raised contact surface 50 is attached. The screw 49 is mounted in the same way as in the other described embodiment in a bone screw 2 which is in turn surgically inserted in the skull 3 of the patient.

On coupling the second coupling part 38 is pushed in through an oblong opening 51 in the first coupling part 39 until the second coupling part's 38 contact surface 44a meets the first coupling part's 39 contact surface 50.

In that position the second coupling part 38 is rotated a quarter turn whereby the cone-shaped flattened contact surface 44 is locked by the locking cylinder 46 and held there in that position by the spring loaded pins 43 pressing against two sides of the second coupling part's square part 42. Because the flexible packing 47 is pressed together on rotation a pressure is obtained on the locking cylinder 46 which tries to press the second coupling part's 38 contact surface 44 against the first coupling part's contact surface 50 whereby the mechanical contact essential for transmission of the sound is maintained between the two coupling parts.

In FIGS. 6a, b, c is shown a further embodiment of a coupling according to the invention. The first coupling part 52 consists, in the same way as in the other embodiment, of an outer, mainly cylindrical frame 53 equipped at its top with a flange 54. At the flange is a plate 55 tightly attached with screws 56. Through the central part of the plate 55, which has thicker material, passes the upper axle-shaped part of a fastening element 57 which is adjustable in the axial direction and which is equipped with a recess 59 on one side. A packing 60, of for example silicon rubber, is placed between the plate's 55 underside and a flange 61 attached to the fastening element's 57 lower part, which flange applies a mainly constant force pushing away between the fastening element 57 and the plate 55.

In FIG. 6b the first coupling part 52 is shown from above so that it is seen how the hole 64 for receiving the second coupling part's 62 coupling element 63 is shaped. At the bottom of that hole 64 is a groove 65 arranged for locking the fastening element 63 of the second coupling part 62 shown in FIG. 6c, which fastening element 63 mainly consists of a circular axle in one end of which a recess 66 is arranged to fit the recess 59 in the fastening element 57. On coupling the first and second coupling part's 52,62 the second coupling part's 62 fastening element 63 is inserted in the first coupling part's 52 hole 64 at such an angle that the second coupling part's recess 66 is used so that its coupling part 63 shall be free from the fastening element's 57 outer part. When the second coupling part's 62 fastening part 63 has reached the bottom of the hole 64 the second coupling part 62 is bent back so that practically no angular difference remains between the first- and second coupling part's central axle. Thereby the hooks formed by the holes grip into each other and as the active element and the packing 60 thus press together a mainly constant pressure is obtained which continuously presses down the point of the second coupling part's 62 coupling element 63 in the groove 65 in the hole 64 which consequently locks the second and the first coupling parts 62, 52 to each other.

Using the above described couplings according to the invention a number of advantages are achieved compared to known technology. Above all a coupling with a low profile is realized which makes it esthetically attractive and insensitive to blows and hits. The coupling is not in the way during sleep and clothing does not snag in it as easily. The coupling cannot unscrew itself either through rotations made by the transmitter or the active element. The coupling is further angle stable, that is because the second coupling's raised parts snap down into the first coupling part's grooves a stable neutral position is obtained.

In FIG. 7a is shown an embodiment of a coupling according to the invention which is relatively easy to disassemble and therefore easily serviced. In the usual way the coupling is limited at the sides by a rotation symmetric frame 70 in the bottom 71 of which is arranged a hole fitting a bone screw 2. The frame's 70 encompassing walls limit a volume 73 placed inside the first coupling part 77. This volume 73 has an opening pointed away from the coupling part's 77 bottom. On the inside of the frame 70 is a groove 78 placed near the edge of the opening. This groove 78 is arranged to hold a flexible element, an O-ring 74 for example of silicon rubber, in position. A spacer 79, for example made of plastic, also equipped with a groove 80 around its perifery, is placed in the volume 73. The spacer 79 is placed in the volume 73 so that the spacer's 79 outer limiting surface 75 mainly coincides with the coupling's outer limiting surface 20. The O-ring 74 allows the spacer 79 certain mobility for action against a force.

In FIG. 7b the form of the spacer 79 is shown in greater detail. A rectangular opening 81 stretches axially through the spacer 79 to allow insertion of a second coupling part 82. In the bottom of the spacer 79 countersunk edges 84 are placed in conjunction with the hole 81 to allow rotation, a quarter turn, and locking of the coupling parts to each other. On rotation of the coupling the spacer 79 is moved a little outward axially whereby a force pressing the coupling parts together is activated by the O-ring's 74 flexibility.

The spacer 79 is further equipped with a locking groove 83 arranged across the hole 81. When rotation of the second coupling part is completed a quarter turn the spacer 79 is pushed down and the second coupling part 82 grips the locking groove 83. Through action of the O-ring 74 the coupling parts are held in this "locked" position until a force stronger than that which locks the parts acts on one of the coupling parts.

In FIG. 7c is shown the second coupling part from the side. Here it is clear that it consists mainly of a contact piece 86 placed on the extreme end of a mainly round axle 85. The contact piece's 86 downward pointing surface is arched among other things to make the coupling "self cleaning." The upper side of the contact piece 86 also has a slightly arched surface which makes rotation and gripping the locking groove 83 easier.

Through the construction of the described coupling parts and the active element a coupling is achieved with a long mechanical life which is also influenced by the coupling together being a rotation movement instead of a simple "snapping mechanism" which is the case for the known coupling. The snap in such a locking mechanism which occurs at the moment of locking and which is uncomfortable for the patient is also avoided. Locking through a rotation movement also protects the sensitive vibration element of the transmitter to which the second coupling part is mechanically attached.

If the transmitter is exposed to loads in the form of hits or bumps, or is overloaded in some other way, it is necessary that the coupling is easily broken, which otherwise could lead to serious consequences such as cracking the skull around the bone screw or the like. Through the construction according to the invention with the second coupling part only somewhat inserted in the first coupling part and in which the fastening element is made in plastic the grips/flanges are dimensioned so that they shall give way at a given previously determined load. Neither does a disadvantageous lever effect occur, partly because the first coupling part's upper part is shaped with partly skew surfaces. This loading limit can be adjusted, in addition to through appropriate choice of material and dimensioning of the gripping flanges thickness, through arranging grooves in the fastening element's upper part which make the gripping flanges give way.

The invention is naturally not limited to the embodiments described above, but instead a number of alternative embodiments are possible within the scope of the invention.

I claim:

1. Coupling, primarily intended for mechanical transmission of sound information from a vibration generating apparatus such as a transducer (8) to the skull of a hearing impaired person, comprising a first coupling part (5,9,29,39,52), tightly anchored in the skull, and a second coupling part (7,17,38,62) attachable to said first part and arranged at the transducer (8), so that at least one vibration transmitting surface is formed between the coupling parts, wherein the vibration transmitting surfaces (18,50) are located inside the outer surface (20) of the first coupling part (9,29,39,52), and said first coupling part (9,29,39,52) is disposed in such a way that the outer surface thereof (20) is located essentially at the same level as the outer surface (22) of the skull.

2. The coupling according to claim 1, wherein the first and the second coupling part are arranged to lock to one another so that one for the coupling part is rotated at a quarter of a turn in relation to the other coupling part.

3. The coupling according to claim 1, wherein an active element (21) is located inside the outer surface (20) of the first coupling part (9,29,39,52) and arranged to apply a constant force in the axial direction of the coupling (1) in such a way that the vibration transmitting surfaces (44,50) of the coupling (1) are pressed against each other and arranged to apply a constant axial force of the coupling (1) parts and thereby on the coupling's (1) vibration transmission surfaces (18,28;44,50).

* * * * *